United States Patent

Bernardi et al.

[11] Patent Number: 4,690,929
[45] Date of Patent: Sep. 1, 1987

[54] ERGOLINES EXHIBITING PROTACTIN SECRETION INHIBITION ACTIVITY

[75] Inventors: Luigi Bernardi, Milan; Laura Chiodini, Busto Arsizio; Sergio Mantegani, Milan; Daniela Ruggieri, Milan; Aldemio Temperilli, Milan; Patricia Salvati, Milan, all of Italy

[73] Assignee: Farmitalia Carlo Erba, Milan, Italy

[21] Appl. No.: 604,041

[22] Filed: Apr. 26, 1984

[30] Foreign Application Priority Data

Apr. 28, 1983 [GB] United Kingdom ............... 8311679
May 27, 1983 [GB] United Kingdom ............... 8314816

[51] Int. Cl.$^4$ ............... A61K 31/48; C07D 457/04
[52] U.S. Cl. ............... 514/288; 514/218; 514/253; 514/254; 540/545; 544/361; 546/67; 546/68; 546/69
[58] Field of Search ............... 546/67, 68, 69; 514/288, 218, 253, 254; 544/361

[56] References Cited

U.S. PATENT DOCUMENTS 3,821,226  6/1974  Fehr et al. ............... 546/67
4,500,712  2/1985  Bernardi et al. ............... 546/67

FOREIGN PATENT DOCUMENTS 32684   7/1981  European Pat. Off.
56358   7/1982  European Pat. Off.
2459630 7/1975  Fed. Rep. of Germany.
2459629 7/1975  Fed. Rep. of Germany.
3240727 5/1983  Fed. Rep. of Germany.
54897   4/1982  German Democratic Rep.
5615181 1/1980  Switzerland.
956261  5/1964  United Kingdom ............... 546/67
2056437 3/1981  United Kingdom ............... 546/67

OTHER PUBLICATIONS

Salvati, et al., "Ergoline Derivatives and their Use", Chem. Abst. 96, 199974 (1982).
Temperilli, et al., "Ergoline Derivatives", Chem. Abst. 98:161005w (1983).
Fehr, et al., "Antihypertensiv wirksame Harnstoff Derivative ... ,", Eur. J. Med. Chem. 1974 pp. 597–601.

Primary Examiner—Donald G. Daus
Assistant Examiner—C. Shen
Attorney, Agent, or Firm—Oblon, Fisher, Spivak, McClelland, & Maier

[57] ABSTRACT

Compounds of formula I:

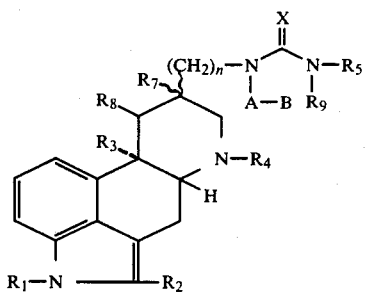

wherein $R_1$ represents a hydrogen atom or a methyl group; $R_2$ represents a hydrogen or halogen atom or a methyl, cyano, $C_1$–$C_4$ alkylthio or phenylthio group; $R_7$ and $R_8$ represent hydrogen atoms and $R_3$ represents a hydrogen atom or a methoxy group, or $R_7$ represents a hydrogen atom and $R_3$ and $R_8$ taken together represent a bond, or $R_3$ represents a hydrogen atom or a methoxy group and $R_7$ and $R_8$ taken together represent a bond; $R_4$ represents a hydrocarbon group having from 1 to 4 carbon atoms; $R_5$ represents a hydrogen atom or a hydrocarbon group hving from 1 to 4 carbon atoms or a phenyl group; X represents an oxygen or sulphur atom or an imino group, $R_9$ represents a hydrogen atom and B represents a cyano, a $C_2$–$C_5$ alkoxycarbonyl or carbamoyl group, or $R_9$ and B taken together represent a

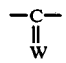

group wherein W represents an oxygen atom or an imino group; A represents a group of the formula $CHR_6$, $CH_2$—$CHR_6$ or $CH$=$CR_6$ group wherein $R_6$ represents a hydrogen atom or a $C_1$–$C_4$ alkyl group; and n is 0, 1 or 2; and their pharmaceutically acceptable salts are disclosed, along with the use of these compounds as antiprolactinic and antihypertensive agents. The preparation of these compounds and pharmaceutical compositions containing them are also described.

7 Claims, No Drawings

ERGOLINES EXHIBITING PROTACTIN SECRETION INHIBITION ACTIVITY

FIELD OF THE INVENTION

The invention relates to ergoline derivatives, to processes for their preparation and to pharmaceutical compositions containing them.

SUMMARY OF THE INVENTION

It is an object of this invention to provide ergoline derivatives exhibiting antihypertensive activity while exhibiting minimal side effects.

It is a further object of this invention to provide ergoline derivatives exhibiting prolactin secretion inhibition activity.

It is still another object of this invention to provide pharmaceutical compositions containing biologically active ergoline derivatives.

It is yet another object of this invention to provide a method of synthesizing biologically active ergoline derivatives.

These and other objects of the invention as will hereinafter become more readily apparent have been accomplished by providing ergoline derivatives having the formula I

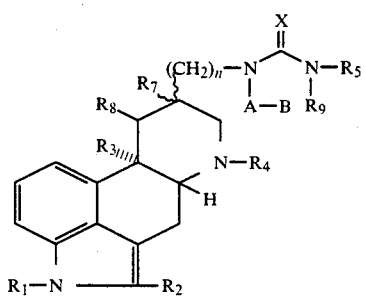

wherein $R_1$ represents a hydrogen atom or a methyl group; $R_2$ represents a hydrogen or halogen atom or a methyl, cyano, $C_1$–$C_4$ alkylthio or phenylthio group; $R_7$ and $R_8$ represent hydrogen atoms and $R_3$ represents a hydrogen atom or a methoxy group, or $R_7$ represents a hydrogen atom and $R_3$ and $R_8$ taken together represent a bond, or $R_3$ represents a hydrogen atom or a methoxy group and $R_7$ and $R_8$ taken together represent a bond; $R_4$ represents a hydrocarbon group having from 1 to 4 carbon atoms; $R_5$ represents a hydrogen atom or a hydrocarbon group having from 1 to 4 carbon atoms or a phenyl group; X represents an oxygen or sulphur atom or an imino group, $R_9$ represents a hydrogen atom and B represents a cyano, a $C_2$–$C_5$ alkoxycarbonyl or carbamoyl group, or $R_9$ and B taken together represents a

group wherein W represents an oxygen atom or an imino group; A represents a group of the formula $CHR_6$, $CH_2$—$CHR_6$ or $CH=CR_6$ group wherein $R_6$ represents a hydrogen atom or a $C_1$–$C_4$ alkyl group; and n is 0, 1 or 2; and pharmaceutically acceptable salts thereof. These compounds, and pharmaceutical compositions containing these compounds, can be used in a method of reducing hypertension which comprises administering such compounds to a human or animal having hypertension.

DESCRIPTION OF THE PREFERRED EMBODIMENTS

The invention provides ergoline derivatives having the formula I

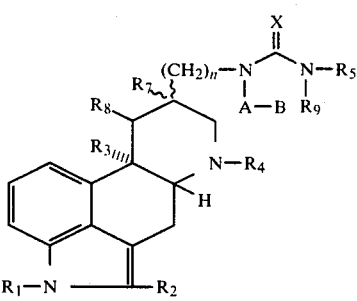

wherein $R_1$ represents a hydrogen atom or a methyl group; $R_2$ represents a hydrogen or halogen atom or a methyl, cyano, $C_1$–$C_4$ alkylthio or phenylthio group; $R_7$ and $R_8$ represent hydrogen atoms and $R_3$ represents a hydrogen atom or a methoxy group, or $R_7$ represents a hydrogen atom and $R_3$ and $R_8$ taken together represent a bond, or $R_3$ represents a hydrogen atom or a methoxy group and $R_7$ and $R_8$ taken together represent a bond; $R_4$ represents a hydrocarbon group having from 1 to 4 carbon atoms; $R_5$ represents a hydrogen atom or a hydrocarbon group having from 1 to 4 carbon atoms or a phenyl group; X represents an oxygen or sulphur atom or an imino group, $R_9$ represents a hydrogen atom and B represents a cyano, a $C_2$–$C_5$ alkoxycarbonyl or carbamoyl group, or $R_9$ and B taken together represent a

group wherein W represents an oxygen atom or an imino group; A represents a group of the formula $CHR_6$, $CH_2$—$CHR_6$ or $CH=CR_6$ group wherein $R_6$ represents a hydrogen atom or a $C_1$–$C_4$ alkyl group;.and n is 0, 1 or 2. In the definition of $R_2$, the term "halogen" should be construed to preferably encompass chlorine and bromine atmos; nevertheless, term "halogen" also encompasses a fluorine atom. In the definition of $R_4$ and $R_5$, a hydrocarbon group having from 1 to 4 carbon atoms is intended to include alkyl, cycloalkyl and unsaturated (both ethylenically and acetylenically unsaturated) groups. Representative moieties include methyl, ethyl, n-propyl, isopropyl, butyl, t-butyl, isobutyl, cyclopropyl, methylcyclopropyl, vinyl, allyl and propargyl.

Pharmaceutically acceptable salts of these ergoline derivatives are included in the invention. "Pharmaceutically acceptable salts" refers to those salts which retain the biological effectiveness and properties of the free bases and which are not biologically or otherwise undesirable. Such salts are formed with inorganic acids such as hydrochloric, hydrobromic, sulfuric, nitric or phosphoric acid and organic acids such as acetic, propionic, glycolic, pyruvic, oxalic, malic malonic, succinic, maleic, furmaric, tartaric, citric, benzoic, cinnamic, mandelic, methanesulfonic, ethanesulfonic, p-toluene sulfonic or salicylic acid.

The substituents $R_1$, $R_2$, $R_3$, $R_7$, $R_8$ and $R_5$ are preferably hydrogen atoms, Preferably $R_4$ is a methyl group, n is 1, B and $R_9$ are taken together and represent a

group. Preferably W and X are oxygen atoms, and A represents a group of the formula —$CH_2$— or —$CH_2$—$CH_2$—; most preferably A is a group of formula —$CH_2$—.

The present invention also provides a process for the preparation of a compound of formula I as described above which includes the step of condensing an ergoline derivative of formula II

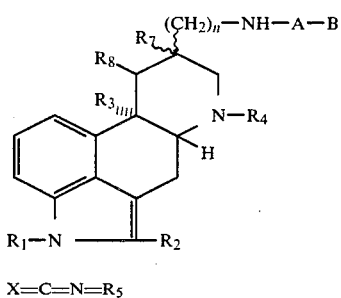

$$X=C=N=R_5 \qquad III$$

wherein $R_1$, $R_2$, $R_3$, $R_4$, $R_7$, $R_8$, A, B and n are as above defined, with a compound of formula III wherein $R_5$ and X are as above-defined. The resultant compounds of formula I wherein $R_9$ is a hydrogen atom may be converted by cyclization into other compounds of formula I wherein $R_9$ and B taken together represent a

group, wherein W is as above-defined. The condensation process may be carried out in a solvent such as water, ethanol, acetic acid or pyridine with or without addition of acid, such as hydrogen chloride, at a temperature of from 50° to 100° C. The cylization may be carried out in the same condensation medium, or by heating in vacuo at 130°-160° C. the isolated compounds of formula I wherein $R_9$=H. When the reaction is over, the crude product can be purified by crystallization or by chromatography.

The ergoline derivatives of the general formula II, the starting materials for the process, are known compounds or can be prepared by established procedures starting from known compounds. According to one preferred method, the compounds of the general formula II wherein A represents a $CH_2$—$CHR_6$ group can be obtained by reacting an appropriate ergoline primary amine with an acryl derivative of formula

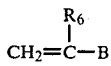

wherein $R_6$ and B are as above defined. Alternatively, a compound of formula

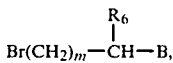

wherein $R_6$ and B are as above defined and m is 0 or 1, can be made to react with an appropriate ergoline primary amine to give the compounds of the general formula II.

The compounds of formula III, the other starting materials for the process, are known compounds and may be generated in situ by reaction of an appropriate salt thereof with an acid, such as hydrochloric acid.

Free base forms of the compounds of formula I may be converted into acid addition salt forms in conventional manner, and salt forms can likewise be converted to free base forms.

The compounds according to the invention and their pharmaceutically acceptable salts exhibit pharmacological activities. For example, they exhibit prolactin secretion inhibition activity as indicated by an inhibition of the implantation of fertilized eggs in the uterus on day 5 after insemination of female rats [according to the principles of E. Fluckiger et al, HANDB. EXP. PHARMAC., 49, 615 (1978)].

In particular the compounds and the salts thereof of the present invention are active as antihypertensive agents. The antihypertensive activity of compounds of the invention has been demonstrated using standard testing procedures, which are reported here for purposes of illustrating the utility of these compounds.

ANTIHYPERTENSIVE ACTIVITY: METHODS

Indirect measurements of systolic blood pressure were carried out in groups of 4 spontaneously hypertensive rats (SHR, Kyoto), 8-10 weeks of age, supplied by Charles River, Italy. The animals were maintained in an environment of 36° C. for 10-15 minutes to allow pulse pressure to be recorded, and then systolic blood pressure and heart rate were measured by indirect tail cuff method using a W+W, BP Recorder, model 8005. The compounds were given orally, suspended in 5% arabic gum, once a day for 4 consecutive days, and measurements were carried out before beginning the treatment and 1 and 5 hours after dosing, in both the first and fourth day of treatment. During doses refer to the free base. Control animals received the vehicle only (0.2 ml/100 g b.w.).

As reference standards, hydralazine (1-5 mg/Kg$^{-1}$ p.o.) and α-methyldopa (30-100 mg.Kg$^{-1}$ p.o.) were also tested. Drug-induced changes in systolic blood pressure and heart rate were calculated as differences from the pretreatment values and reported as means of 4 rats.

ANTIHYPERTENSIVE ACTIVITY: RESULTS

Tables 1 and 2 show the results concerning the presently claimed compounds along with data concerning control vehicle and two reference standards, hydralazine and α-methyldopa. Systolic blood pressure (SBP) and heart rate (HR) remained stable throughout the duration of the experiment in vehicle-treated rats; on the other hand, all compounds of the invention were very active in reducing SBP in doses ranging from 1 to 20 mg.Kg$^{-1}$ p.o. This effect was not accompanied by a reflex increased in HR, while a moderate decrease in HR was instead observed with some of them. The antihypertensive activity of all the compounds had a prompt onset and remained very marked at all the experimental times. The effects were similar on the 1st and 4th days of treatment showing tachyphylaxis not to occur with compounds of the invention. In particular the compounds prepared in Examples 1 and 3 below both showed a very marked and prolonged activity without substantially modifying HR.

Comparison with the reference standards showed how the compounds of Examples 4, 5, 8, 9, 12, 13, 16, 19, 23, 24 and 28 (tested in doses ranging from 1 to 7.5 mg.Kg$^{-1}$ p.o.) were more active than hydralazine (1–5 mg.Kg$^{-1}$ p.o.) and α-methyldopa (30–100 mg.Kg$^{-1}$ p.o.) without inducing the reflex increase in HR observed with these latter drugs.

TABLE 1

Effects on systolic blood pressure (SBP) in SHR rats. Mean differences from pretreatment values (mmHg) (4 rats per group) are reported.

| Compound | Dose mg. Kg$^{-1}$ p.o. | Changes in S.B.P. (Δ mmHg) | | | |
|---|---|---|---|---|---|
| | | 1st day | | 4th day | |
| | | 1 h post drug | 5 h post drug | 1 h post drug | 5 h post drug |
| Vehicle | — | +2.5 | −7.5 | −6.4 | −5.0 |
| Prepared in Ex. 1 | 20 | −90.0 | −62.5 | −62.5 | −46.2 |
| Prepared in Ex. 3 | 20 | −60.0 | −72.5 | −90.0 | −62.5 |
| Prepared in Ex. 4 | 20 | −53.3 | −45.0 | −42.5 | −50.0 |
| Prepared in Ex. 4 | 5 | −35.0 | −40.0 | −43.7 | −45.0 |
| Prepared in Ex. 5 | 7.5 | −55.0 | −56.2 | −55.0 | −53.7 |
| Prepared in Ex. 8 | 20 | −30.0 | −10.0 | −36.2 | −37.5 |
| Prepared in Ex. 9 | 7.5 | −51.2 | −65.0 | −82.5 | −55.0 |
| Prepared in Ex. 12 | 7.5 | −52.5 | −38.7 | −37.5 | −41.2 |
| Prepared in Ex. 13 | 7.5 | −37.5 | −26.2 | −50.0 | −31.7 |
| Prepared in Ex. 16 | 1 | −20.0 | −28.7 | −43.7 | −52.5 |
| Prepared in Ex. 19 | 15 | −50.0 | −33.7 | −62.5 | −23.7 |
| Prepared in Ex. 23 | 20 | −51.2 | −60.0 | −85.0 | −72.5 |
| Prepared in Ex. 24 | 5 | −38.7 | −66.7 | −41.7 | −38.3 |
| Prepared in Ex. 28 | 1 | −27.5 | −31.2 | −70.0 | −30.0 |
| Hydralazine | 1 | −5.1 | −15.7 | −5.0 | −0.3 |
| | 5 | −40.2 | −20.0 | −20.4 | −7.0 |
| α-Methyldopa | 30 | −10.4 | −20.1 | −10.0 | +0.5 |
| | 100 | −10.0 | −25.4 | −20.2 | −25.0 |

TABLE 2

Effects on heart rate (HR) in SHR rats. Mean differences from pretreatment values (beats/min) are reported (4 rats per group).

| Compound | Dose mg. Kg$^{-1}$ p.o. | Changes in H.R. (beats/min) | | | |
|---|---|---|---|---|---|
| | | 1st day | | 4th day | |
| | | 1 h post drug | 5 h post drug | 1 h post drug | 5 h post drug |
| Vehicle | — | −5.0 | +12.0 | −10.0 | −19.0 |
| Prepared in Ex. 1 | 20 | +4.0 | −40.0 | −33.0 | −8.0 |
| Prepared in Ex. 3 | 20 | −20 | −10.0 | −25.0 | −7.0 |
| Prepared in Ex. 4 | 20 | +13.0 | +23.0 | −11.0 | −40.0 |
| Prepared in Ex. 4 | 5 | −15.0 | −30.0 | −40.0 | −23.0 |
| Prepared in Ex. 5 | 7.5 | −37.0 | −20.0 | −42.0 | −10.0 |
| Prepared in Ex. 8 | 20 | −13.0 | +0.4 | +40.0 | −20.0 |
| Prepared in Ex. 9 | 7.5 | −60.0 | −32.0 | −75.0 | −28.0 |
| Prepared in Ex. 12 | 7.5 | −40.0 | −28.0 | +8.0 | +2.0 |
| Prepared in Ex. 13 | 7.5 | +13.0 | −55.0 | +37.0 | −20.0 |
| Prepared in Ex. 16 | 1 | −28.0 | −8.0 | −60.0 | −35.0 |
| Prepared in Ex. 19 | 15 | −18.0 | −32.0 | −35.0 | +15.0 |
| Prepared in Ex. 23 | 20 | −8.0 | +17 | +42.0 | −18.0 |
| Prepared in Ex. 24 | 5 | −23.0 | +17.0 | +30.0 | −27.0 |
| Prepared in Ex. 28 | 1 | −13.0 | −23.0 | +15.0 | −15.0 |
| Hydralazine | 1 | +30.0 | +35.0 | +25.0 | +15.0 |
| | 5 | +40.0 | +45.0 | +18.0 | +15.0 |
| α-Methyldopa | 30 | +35.0 | +40.0 | +45.0 | +30.0 |
| | 100 | +70.0 | +40.0 | +50.0 | +10.0 |

The invention further comprises a pharmaceutical composition containing a therapeutically effective amount of a compound of formula I or a pharmaceutically acceptable salt thereof in admixture with a pharmaceutically acceptable diluent or carrier. As used herein, the term "effective amount" encompasses those amounts which yield the desired activity (e.g., reduction in blood pressure) without causing adverse side effects (e.g., undesirable increase in heart rate). For example, an effective dosage is preferably in the range of about 0.001 to 0.5 mg/Kg/day, more preferably 0.01 to 0.25 mg/Kg/day.

The administration of compounds I and their non-toxic pharmaceutically acceptable, acid-addition salts or mixtures thereof may be achieved either parenterally or orally, preferably orally. The pharmaceutical carriers which are typically employed with the compounds of the invention may be solid or liquid and are generally selected dependent on the planned manner of administration. Thus, for example, solid carriers include lactose, sucrose, gelatin and agar and the like, while liquid carriers include water, syrup, peanut oil and olive oil and the like. The combination of the selected compound and the carrier may be fashioned into numerous acceptable forms such as tablets, capsules, suppositories, solutions, emulsion, powders and syrups.

The following examples are intended to illustrate the invention and are not to be considered limiting thereof, unless specifically so stated.

EXAMPLE 1

6-Methyl-8β-[(1H,3H)-2,4-dioxo-dihydro-1-pyrimidinylmethyl]-ergoline

I: $R_1=R_2=R_3=R_7=R_8=H$, $R_4=CH_3$, $n=1$, $A=CH_2CHR_6$, $R_6=H$, B and

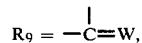

W=X=O, $R_5=H$

A mixture of 5.1 g of 8β-aminomethyl-6-methyl-ergoline and 1.8 ml of methyl acrylate in 100 ml of methanol was refluxed for four hours. The solvent was evaporated off under reduced pressure, and the residue was crystallized from diethyl ether to give 6 g of 6-methyl-8β-[N-(2-methoxycarbonylethyl)-aminomethyl]-ergoline (II: $R_1=R_2=R_3=R_7=R_8=H$, $R_4=CH_3$, $n=1$, $A=CH_2-CHR_6$, $R_6=H$, $B=COOCH_3$) melting at 130°–132° C. To a solution of 2.86 g of potassium cyanate in 30 ml of water, a solution of 6 g of 6-methyl-8β-[N-(2-methoxycarbonylethyl)-aminomethyl]-ergoline in 120 ml of water and 35 ml of 1N hydrochloric acid was added. This reaction mixture was heated for four hours at 80° C. and allowed to stand overnight at room temperature. The solid separated out and was filtered off and recrystallized from ethanol to give 4.5 g of the title compound melting at 330° C. with decomposition.

EXAMPLE 2

6-Methyl-8β-[N-(2-methoxycarbonylethyl)-N-carbamoylaminomethyl]-ergoline

I: $R_1=R_2=R_3=R_5=H$, $R_4=CH_3$, $n=1$,
$A=CH_2CHR_6$, $R_6=H$, $X=O$, $B=COOCH_3$,
$R_7=R_8=R_9=H$

A mixture of 8.5 g of 6-methyl-8β-[N-(2-methoxycarbonyl-ethyl)aminomethyl]-ergoline (II: $R_1=R_2=R_3=H$, $R_4=CH_3$, $n=1$, $A=CH_2-CHR_6$, $R_6=H$, $B=COOCH_3$; prepared as described in Example 1) and 2.86 g of potassium cyanate in 120 ml of water and 35 ml of 1N hydrochloric acid was heated at 60° C. for one hour. The solution was then neutralized with 1N sodium hydroxide and extracted with chloroform. The organic layer was evaporated off, and the residue was purified by column chromatography on silica gel, to give 6.5 g of the title compound. Rf in ethyl acetate:-dimethylformamide:n-butanol:pyridine (4:3:3:1 by volume)=0.45; MS (F.D.): 384 (M+), 352 (M+—CH$_3$OH).

EXAMPLE 3

6-Methyl-8β-(2,4-dioxo-1-imidazolidinyl-methyl)-ergoline

I: R$_1$=R$_2$=R$_3$=H, R$_4$=CH$_3$, n=1, A=CHR$_6$, R$_6$=H, R$_7$=R$_8$=R$_5$=H B and

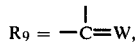

W=X=O

A solution of 1.3 ml of ethyl bromoacetate in 30 ml of dimethylformamide was added to a warmed solution of 6 g of 8β-aminomethyl-6-methyl-ergoline in 90 ml of dimethylformamide. At the end of the reaction, the solution was reduced in volume by evaporation in vacuo, poured into iced water and extracted with chloroform. The organic layer was removed in vacuo and the residue was purified by column chromatography on silica gel, using ethyl acetate:methanol (9:1 by volume) as eluent, to give 3.5 g of 6-methyl-8β-(N-ethoxycarbonylmethyl-aminomethyl)-ergoline (II: R$_1$=R$_2$=R$_3$=H, R$_4$=CH$_3$, n=1, A=CHR$_6$, R$_6$=H, B=CO$_2$C$_2$H$_5$), m.p. 174°-176° C., after crystallization from diethyl ether. 3.5 of 6-methyl-8β-(N-ethoxycarbonylmethyl-aminomethyl)-ergoline were treated with 1.75 g of potassium cyanate, as described in Example 1, and the title compound, m.p. >300° C., was obtained in 72% yield.

EXAMPLE 4

6-Methyl-8β-[N-(2-methoxycarbonylethyl)-N-methylcarbamoyl-aminomethyl]-ergoline

I: R$_1$=R$_2$=R$_3$=H, R$_4$=CH$_3$, n=1, A=CH$_2$CHR$_6$, R$_6$=R$_7$=R$_8$=R$_9$=H, R$_5$=CH$_3$, B=COOCH$_3$, X=O

A mixture of 8.5 g of 6-methyl-8β-[N-(2-methoxycarbonylethyl)-aminomethyl]-ergoline (prepared as described in Example 1) and 2.95 ml of methyl isocyanate in 100 ml of pyridine was heated at 60° C. for one hour. After evaporating off the solvent, the residue was crystallized from methanol to give 8.5 of the title compound, m.p. 140°-142° C.

EXAMPLE 5

6-Methyl-8β-[(1H,3H)-2,4-dioxo-3-methyl-dihydro-1-pyrimidinyl-methyl]-ergoline

I: R$_1$=R$_2$=R$_3$=H, R$_4$=CH$_3$, n=1, A=CH$_2$CHR$_6$, R$_6$=H, B and

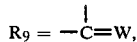

R$_5$=CH$_3$, R$_7$=R$_8$=H, X=W=O

On heating for one hour at 145° C. in vacuo, 6-methyl-8β-[N-(2-methoxycarbonylethyl)-N-methylcarbomoyl-aminomethyl]-ergoline (prepared as described in example 4) gave 6.5 g of the title compound, m.p. 118°-120° C., after crystallization from methanol.

EXAMPLE 6

6-methyl-8β-(N-ethoxycarbonylmethyl-N-methylcarbamoyl-aminomethyl)-ergoline

I: R$_1$=R$_2$=R$_3$=H, R$_4$=CH$_3$, n=1, A=CHR$_6$, R$_6$=R$_7$=R$_8$=R$_9$=H, R$_5$=CH$_3$, B=COOC$_2$H$_5$, X=O

Operating as in Example 4, but employing 6-methyl-8β-(N-ethoxycarbonylmethyl-aminoethyl)-ergoline (prepared as described in Example 3) instead of 6-methyl-8β-[N-(2-methoxycarbonylethyl)-aminomethyl]-ergoline, the title compound, m.p. 165°-167° C., was obtained.

EXAMPLE 7

6-Methyl-8β-(2,4-dioxo-3-methyl-1-imidazolidinylmethyl)-ergoline

I: R$_1$=R$_2$=R$_3$=H, R$_4$=CH$_3$, n=1, A=CHR$_6$, R$_6$=R$_7$=R$_8$=H, R$_5$=CH$_3$, B and

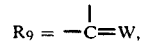

W=X=O

From 6-methyl-8-β-(N-ethoxycarbonylmethyl-N-methylcarbamoylaminomethyl)-ergoline, the title compound, m.p. 250° C. with decomposition, was obtained in 77% yield by heating in vacuo for one hour at 140° C.

EXAMPLE 8

6-Methyl-8β-[N-(2-methoxycarbonylethyl)-N-propylcarbamoyl-aminomethyl]-ergoline

I: R$_1$=R$_2$=R$_3$=H, R$_4$=CH$_3$, R$_5$=CH$_2$CH$_2$CH$_3$, n=1, A=CH$_2$CHR$_6$, R$_6$=R$_7$=R$_8$=R$_9$=H, X=O, B=COOCH$_3$

The title compound was prepared as described in Example 4, but propyl isocyanate was used instead of methyl isocyanate. The yield was 85% and the m.p. was 130°-132° C.

EXAMPLE 9

6-Methyl-8β-[(1H,3H)-2,4-dioxo-3-propyl-dihydro-1-pyrimidinyl-methyl]-ergoline

I: R$_1$=R$_2$=R$_3$=H, R$_4$=CH$_3$, n=1, A=CH$_2$CHR$_6$, R$_6$=R$_7$=R$_8$=H, R$_5$=CH$_2$CH$_2$CH$_3$, B and

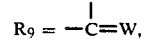

X=W=O

Operating as in Example 5, but employing 6-methyl-8β-[N-(2-methoxycarbonylethyl)-N-propylcarbamoyl-aminomethyl)]-ergoline (prepared in Example 8) instead of 6-methyl-8β-[N-(2-methoxycarbonylethyl)-N-methylcarbamoyl-aminomethyl]-ergoline, the title compound, m.p. 201°-202° C., was obtained in 70% yield.

EXAMPLE 10

6-Methyl-8β-[N-(2-methoxycarbonylethyl)-N-isopropylcarbamoyl-aminomethyl]-ergoline I: $R_1=R_2=R_3=H$, $R_4=CH_3$, n=1, $A=CH_2CHR_6$, $R_5=CH(CH_3)_2$ $R_6=R_7=R_8=R_9=H$, $B=COOCH_3$, $X=O$ Operating as in Example 4, but employing isopropyl isocyanate instead of methyl isocyanate, the title compound, m.p. 112°–115° C., was obtained.

EXAMPLE 11

6-Methyl-8β-[(1H,3H)-2,4-dioxo-3-isopropyl-dihydro-1-pyrimidinyl-methyl]-ergoline I: $R_1=R_2=R_3=H$, $R_4=CH_3$, n=1, $A=CH_2CHR_6$, $R_6=R_7=R_8=H$, $R_5=CH(CH_3)_2$, B and

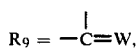

$X=W=O$

From 6-methyl-8β-[N-(2-methoxycarbonylethyl)-N-isopropylcarbamoyl-aminomethyl]-ergoline (prepared in Example 10), the title compound (m.p. 175°–177° C.) was obtained in 60% yield by heating for 2 hours at 150° C.

EXAMPLE 12

6-Methyl-8β-[N-ethoxycarbonylmethyl-N-propylcarbamoylaminomethyl]-ergoline

I: $R_1=R_2=R_3=H$, $R_4=CH_3$, $R_5=CH_2CH_2CH_3$, n=1, $A=CHR_6$, $R_6=R_7=R_8=R_9=H$, $X=O$, $B=COOCH_2CH_3$

Operating as in Example 6, but employing propyl isocyanate instead of methyl isocyanate, the title compound, m.p. 109°–110° C., was obtained in 80% yield.

EXAMPLE 13

6-Methyl-8β-(2,4-dioxo-3-propyl-1-imidazolidinyl)-methyl)-ergoline

I: $R_1=R_2=R_3=H$, $R_4=CH_3$, n=1, $A=CHR_6$, $R_6=R_7=R_8=H$, $R_5=CH_2CH_2CH_3$ B and

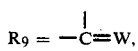

$X=W=O$

From 6-methyl-8β-[N-ethoxycarbonylmethyl-N-propylcarbamoyl-aminomethyl]-ergoline prepared in Example 12, the title compound, m.p. 188°–190° C., was obtained in 68% yield by heating in vacuo for one hour at 140° C.

EXAMPLE 14

6-Methyl-8β-(N-ethoxycarbonylmethyl-N-isopropyl-carbamoyl-aminomethyl)-ergoline

I: $R_1=R_2=R_3=H$, $R_4=CH_3$, n=1, $A=CHR_6$, $R_6=R_7=R_8=R_9=H$, $R_5=CH(CH_3)_2$, $B=COOC_2H_5$, $X=O$

Operating as in Example 6, but employing isopropyl isocyanate instead of methyl isocyanate, the title compound, m.p. 118°–120° C., was obtained.

EXAMPLE 15

6-Methyl-8β-(2,4-dioxo-3-isopropyl-1-imidazolidinyl-methyl)-ergoline

I: $R_1=R_2=R_3=H$, $R_4=CH_3$, n=1, $A=CHR_6$, $R_6=R_7=R_8=H$ $R_5=CH(CH_3)_2$ B and

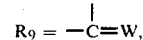

$X=W=O$

Starting from 6-methyl-8β-(N-ethoxycarbonylmethyl-N-isopropylcarbamoyl-aminomethyl)-ergoline (prepared in Example 14), the title compound (m.p. 210°–212° C.) was obtained in 75% yield by heating in vacuo for 2 hours at 160° C.

EXAMPLE 16

6-Methyl-8β-{2-[(1H,3H)-2,4-dioxo-dihydro-1-pyrimidinyl]-ethyl}-ergoline

I: $R_1=R_2=R_3=H$, $R_4=CH_3$, n=2, $A=CH_2CHR_6$, $R_5=R_6=R_7=R_8=H$, B and

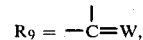

$W=X=O$

Operating as in Example 1, but employing 8β-aminoethyl-6-methyl-ergoline instead of 8β-aminomethyl-6-methyl-ergoline, the title compound, m.p. 140°–142° C., was obtained in 74% yield.

EXAMPLE 17

6-Methyl-8β-[2-(2,4-dioxo-1-imidazolidinyl)-ethyl]-ergoline

I: $R_1=R_2=R_3=H$, $R_4=CH_3$, n=2, $A=CHR_6$, $R_5=R_6=R_7=R_8=H$, B and

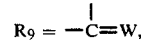

$X=W=O$

Operating as in Example 3, but employing 8β-aminoethyl-6-methyl-ergoline instead of 8β-aminomethyl-6-methyl-ergoline, the title compound, m.p. 242°–244° C., was obtained in 68% yield.

EXAMPLE 18

6-Methyl-8β-[(1H,3H)-2,4-dioxo-dihydro-1-pyrimidinyl]-ergoline

I: $R_1=R_2=R_3=H$, $R_4=CH_3$, n=0, $A=CH_2CHR_6$, $R_5=R_6=R_7=R_8=H$, B and

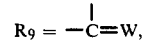

$X=W=O$

Operating as in Example 1, but employing 8β-amino-6-methyl-ergoline instead of 8β-aminomethyl-6-methyl-ergoline, the title compound, m.p. 312°–314° C., was obtained in 79% yield.

EXAMPLE 19

6-Methyl-8β-(2,4-dioxo-1-imidazolidinyl)-ergoline

I: $R_1=R_2=R_3=H$, $R_4=CH_3$, $n=0$, $A=CHR_6$,
$R_5=R_6=R_7=R_8=H$, B and

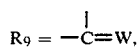

X=W=O

Operating as in Example 3, but employing 8β-amino-6-methyl-ergoline instead of 8β-aminomethyl-6-methyl-ergoline, the title compound, m.p. 295°–297° C., was obtained in 80% yield.

EXAMPLE 20

1,6-Dimethyl-8β-[(1H,3H)-2,4-dioxo-dihydro-1-pyrimidinyl-methyl]-ergoline

I: $R_2=R_3=R_5=R_6=R_7=R_8=H$, $R_1=R_4=CH_3$,
$n=1$, $A=CH_2CHR_6$, B and

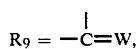

X=W=O

Operating as in Example 1, but employing 8β-aminomethyl-1,6-dimethyl-ergoline instead of 8β-aminomethyl-6-methyl-ergoline, the title compound, m.p. 314°–316° C., was obtained in 75% yield.

EXAMPLE 21

1,6-Dimethyl-8β-(2,4-dioxo-1-imidazolidinyl-methyl)-ergoline

I: $R_2=R_3=R_5=R_6=R_7=R_8=H$, $R_1=R_4=CH_3$,
$n=1$, $A=CHR_6$, B and

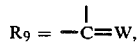

X=W=O

Operating as in Example 3, but employing 8β-aminomethyl-1,6-dimethyl-ergoline instead of 8β-aminomethyl-6-methyl-ergoline, the title compound, m.p. 292°–294° C., was obtained in 65% yield.

EXAMPLE 22

6-Methyl-10-methoxy-8β-(2,4-dioxo-1-imidazolidinyl-methyl)-ergoline

I: $R_1=R_2=R_5=R_6=R_7=R_8=H$, $R_3=OCH_3$,
$R_4=CH_3$, $n=1$, $A=CHR_6$, B and

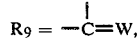

X=W=O

Operating as in Example 3, but employing 8β-aminomethyl-6-methyl-10-methoxy-ergoline instead of 8β-aminomethyl-6-methyl-ergoline, the title compound, m.p. 234°–236° C., was obtained in 68% yield.

EXAMPLE 23

6-Methyl-8β-[(1H,3H)-2,4-dioxo-1-pyrimidinyl-methyl]-ergoline

I: $R_1=R_2=R_3=R_5=R_6=R_7=R_8=H$, $R_4=OCH_3$,
$n=1$, $A=CH=CR_6$, B and

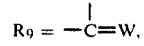

X=W=O

Operating as in Example 1, but employing 6-methyl-6β-[(3-acrylic acid ethyl ester)-3-amino-methyl]-ergoline instead of 6-methyl-8β-[N-2-methoxycarbonylethyl)-aminomethyl]-ergoline, the title compound, m.p. >320° C., was obtained in 48% yield.

EXAMPLE 24

6-Methyl-8β-[(1H)-2-thioxo-4-oxo-tetrahydro-1-pyrimidinyl-methyl]-ergoline

I: $R_1=R_2=R_3=R_5=R_6=R_7=R_8=H$, $R_4=CH_3$,
$n=1$, $A=CH_2CHR_6$, B and

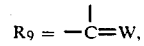

W=O, X=S

Operating as in Example 1, but employing potassium thiocyanate instead of potassium cyanate, the title compound, m.p. >300° C., was obtained in 58% yield.

EXAMPLE 25

6-Methyl-8β-[(1H)-2-thioxo-4-oxo-3-methyl-tetrahydro-1-pyrimidinyl-methyl]-ergoline I: $R_1=R_2=R_3=R_6=R_7=R_8=H$, $R_4=R_5=CH_3$,
$n=1$, $A=CH_2CHR_6$, B and

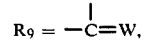

W=O, X=S

Operating as in Example 1, but employing methyl isothiacyanate instead of potassium cyanate, the title compound, m.p. 266°–268° C., was obtained in 74% yield.

EXAMPLE 26

6-n-Propyl-8β-[(1H)-2-thioxo-4-oxo-3-methyl-tetrahydro-1-pyrimidinyl-methyl]-ergoline I: $R_1=R_2=R_3=R_6=R_7=R_8=H$, $R_4=n-C_3H_7$,
$R_5=CH_3$, $n=1$, $A=CH_2CHR_6$, B and

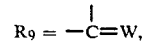

W=O, X=S

Operating as in Example 25, but employing 8β-aminomethyl-6-n-propyl-ergoline instead of 8β-aminomethyl-6-methyl-ergoline, the title compound was obtained in 63% yield.

EXAMPLE 27

6-Allyl-8β-[(1H)-2-thioxo-4-oxo-3-methyl-tetrahydro-1-pyrimidinyl-methyl]-ergoline I: $R_1=R_2=R_3=R_6=R_7=R_8=H$, $R_4=$allyl, $R_5=CH_3$, $n=1$, $A=CH_2CHR_6$, B and

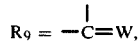

W=O, X=S

Operating as in Example 25, but employing 8β-aminomethyl-6-allyl-ergoline instead of 8β-aminomethyl-6-methyl-ergoline, the title compound was obtained in 77% yield.

EXAMPLE 28

6-Methyl-8β-(2-thioxo9-4-oxo-3-methyl-1-imidazolidinyl-methyl)-ergoline

I: $R_1=R_2=R_3=R_6=R_7=R_8=H$, $R_4=R_5=CH_3$, $n=1$, $A=CHR_6$, B and

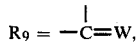

W=O, X=S

Operating as in Example 3, but employing methyl isothiocyanate instead of potassium cyanate, the title compound, m.p. 263°–265° C., was obtained in 83% yield.

EXAMPLE 29

6-Propyl-8β-(2-thioxo-4-oxo-3-methyl-1-imidazolidinyl-methyl)-ergoline

I: $R_1=R_2=R_3=R_6=R_7=R_8=H$, $R_4=$n—$C_3H_7$, $R_5=CH_3$, $n=1$, $A=CHR_6$, B and

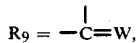

W=O, X=S

Operating as in Example 28, but employing 8β-aminomethyl-6-propyl-ergoline instead of 8β-aminomethyl-6-methyl-ergoline, the title compound was obtained in 88% yield.

EXAMPLE 30

6-Allyl-8β-(2-thioxo-4-oxo-3-methyl-1-imidazolidinyl-methyl)-ergoline

I: $R_1=R_2=R_3=R_6=R_7=R_8=H$, $R_4=$allyl, $R_5=CH_3$, $n=1$, $A=CHR_6$, B and

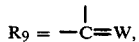

W=O, X=S

Operating as in Example 28, but employing 8β-aminomethyl-6-allyl-ergoline instead of 8β-aminomethyl-6-methyl-ergoline, the title compound was obtained in 69% yield.

EXAMPLE 31

6-Methyl-8β-[N-(2-cyanoethyl)-N-carbamoyl-aminomethyl]-ergoline

I: $R_1=R_2=R_3=R_5=R_6=R_7=R_8=R_9=H$, $R_4=CH_3$, $n=1$, $A=CH_2CHR_6$, X=O, B=CN

Operating as in Example 1, but employing acrylonitrile instead of methyl acrylate, 6-methyl-8β-[N-(2-cyanoethyl)-aminomethyl]-ergoline (m.p. 169°–171° C.) was obtained in 80% yield. From this operating as in Example 2, the title compound, m.p. 252°–254° C., was obtained.

EXAMPLE 32

6-Methyl-8β-[(1H,3H)-2-oxo-4-imino-dihydro-1-pyrimidinyl-methyl]-ergoline

I: $R_1=R_2=R_3=R_5=R_6=R_7=R_8=H$, $R_4=CH_3$, $n=1$, $A=CH_2CHR_6$, B and

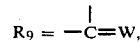

W=NH, X=O

The compound prepared in Example 31, on heating for one hour at 150° C., in vacuo, gave the title compound, m.p. 248°–250° C., in 45% yield.

EXAMPLE 33

2-Bromo-6-methyl-8β-(2,4-dioxo-1-imidazolidinyl-methyl)-ergoline

I: $R_1=R_2=R_3=R_5=R_6=R_7=R_8=H$, $R_2=Br$, $R_4=CH_3$, $n=1$, $A=CHR_6$, B and

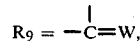

X=W=O

Operating as in Example 3, but employing 8β-aminomethyl-2-bromo-6-methyl-ergoline instead of 8β-aminomethyl-6-methyl-ergoline, the title compound, m.p. 279°–281° C., was obtained in 64% yield.

EXAMPLE 34

2,6-Dimethyl-8β-(2,4-dioxo-1-imidazolindinyl-methyl)-ergoline

I: $R_1=R_2=R_3=R_5=R_6=R_7=R_8H$, $R_2=R_4=CH_3$, $n=1$, $A=CHR_6$, B and

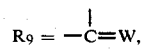

X=W=O

Operating as in Example 3, but employing 8β-aminomethyl-2,6-dimethyl-ergoline instead 8β-aminoethyl-6-methyl-ergoline, the title compound, m.p. 215°–217° C., was obtained in 75% yield.

EXAMPLE 35

2-Thiomethyl-6-methyl-8β-(2,4-dioxo-1-imidazolidinyl-methyl)-ergoline

I: $R_1=R_3=R_5=R_6=R_7=R_8=H$, $R_2=SCH_3$, $R_4=CH_3$, n=1, A=$CHR_6$, B and

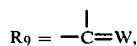

X=W=O

Operating as in Example 3, but employing 8β-aminomethyl-2-thiomethyl-6-methyl-ergoline, the title compound, m.p. 255°–257° C., was obtained in 62% yield.

EXAMPLE 36

6-n-Propyl-8β-(2,4-dioxo-1-imidazolidinyl-methyl)-ergoline

I: $R_1=R_2=R_3=R_5=R_6=R_7=R_8=H$, $R_4=nC_3H_7$, n=1, A=$CHR_6$, B and

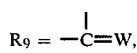

X=W=O

Operating as in Example 3, but employing 8β-aminomethyl-6-n-propyl-ergoline instead of 8β-aminomethyl-6-methyl-ergoline, the title compound, m.p. 168°–170° C., was obtained in 80% yield.

EXAMPLE 37

6-Methyl-8α-(2,4-dioxo-1-imidazolidinyl-methyl)-ergoline

I: $R_1=R_2=R_3=R_5=R_6=R_7=R_8=H$, $R_4=CH_3$, n=1, A=$CHR_6$, B and

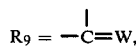

X=W=O

Operating as in Example 3, but employing 8α-aminomethyl-6-methyl-ergoline instead of 8β-aminomethyl-6-methyl-ergoline, the title compound, m.p. 199°–201° C., was obtained in 58% yield.

EXAMPLE 38

6-Methyl-8-[(1H,3H)-2,4-dioxo-dihydro-1-pyrimidinyl-methyl]-8,9-didehydro-ergoline I: $R_1=R_2=R_3=R_5=R_6=H$, $R_4=CH_3$, $R_7$ and $R_8$=bond, n=1, A=$CH_2CHR_6$, B and

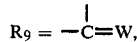

X=W=O

Operating as in Example 1 but employing 8-aminomethyl-6-methyl-8,9-didehydro-ergoline instead of 8β-aminomethyl-6-methyl-ergoline, the title compound, m.p. 190°–192° C., was obtained in 63% yield.

EXAMPLE 39

6-Methyl-8-(2,4-dioxo-1-imidazolidinyl-methyl)-8,9-didehydro-ergoline

I: $R_1=R_2=R_3=R_5=R_6=H$, $R_4=CH_3$, $R_7$ and $R_8$=bond, n=1, A=$CHR_6$, B and

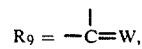

X=W=O

Operating as in Example 3, but employing 8-aminomethyl-6-methyl-8,9-didehydro-ergoline instead of 8β-aminomethyl-6-methyl-ergoline, the title compound, m.p. 204°–206° C., was obtained in 72% yield.

EXAMPLE 40

6-Methyl-8β-[(1H,3H)-2,4-dioxo-dihydro-1-pyrimidinyl-methyl]-9,10-didehydro-ergoline I: $R_1=R_2=R_5=R_6=R_7=H$, $R_3$ and $R_8$=bond, $R_4=CH_3$, n=1, A=$CH_2CHR_6$, B and

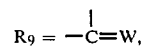

X=W=O

Operating as in Example 1, but employing 8β-aminomethyl-6-methyl-9,10-didehydro-ergoline, instead of 8β-aminomethyl-6-methyl-ergoline, the title compound, m.p. 290°–292° C., was obtained in 77% yield.

EXAMPLE 41

6-Methyl-8β-(2,4-dioxo-1-imidazolidinyl-methyl)-9,10-didehydro-ergoline

I: $R_1=R_2=R_5=R_6=R_7=H$, $R_3$ and $R_8$=bond, $R_4=CH_3$, n=1, A=$CHR_6$, B and

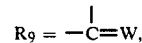

X=W=O

Operating as in Example 3 but employing 8β-aminomethyl-6-methyl-9,10-didehydro-ergoline instead of 8β-aminomethyl-6-methyl-ergoline, the title compound, m.p. 282°–284° C., was obtained in 78% yield.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A compound of formula I:

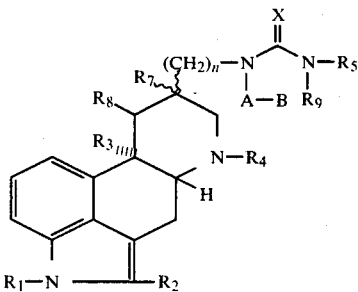

wherein $R_1$ represents a hydrogen atom or a methyl group; $R_2$ represents a hydrogen or halogen atom or a methyl, cyano, $C_1$-$C_4$ alkylthio or phenylthio group; $R_7$ and $R_8$ represent hydrogen atoms and $R_3$ represents a hydrogen atom or a methoxy group, or $R_7$ represents a hydrogen atom and $R_3$ and $R_8$ taken together represent a bond, or $R_3$ represents a hydrogen atom or a methoxy group and $R_7$ and $R_8$ taken together represent a bond; $R_4$ represents a alkyl, alkenyl, alkynyl, cycloalkyl group having from 1 to 4 carbon atoms; $R_5$ represents a hydrogen atom or a alkyl, alkenyl, alkynyl, cycloalkyl group having from 1 to 4 carbon atoms or a phenyl group; X represents an oxygen or sulphur atom or an imino group, $R_9$ represents a hydrogen atom and B represents a cyano, a $C_2$-$C_5$ alkoxycarbonyl or carbamoyl group, or $R_9$ and B taken together represent a

group wherein W represents an oxygen atom or an imino group; A represents a group of the formula $CHR_6$, $CH_2$—$CHR_6$ or $CH=CR_6$ group wherein $R_6$ represents a hydrogen atom or a $C_1$-$C_4$ alkyl group; and n is 0, 1 or 2; or a pharmaceutically acceptable salt thereof.

2. A compound according to claim 1, wherein $R_1$ is a hydrogen atom or a methyl group;

$R_2$ is a hydrogen or bromine atom or a methyl or thiomethyl group;

$R_7$ and $R_8$ represent hydrogen atoms and $R_3$ represents a hydrogen atom or a methoxy group, or $R_7$ represents a hydrogen atom and $R_3$ and $R_8$ taken together represent a bond, or $R_3$ represents a hydrogen atom and $R_7$ and $R_8$ taken together represent a bond;

$R_4$ represents a $C_1$-$C_4$ alkyl or a $C_2$-$C_4$ alkenyl group;

X represents an oxygen or a sulphur atom, $R_5$ represents a hydrogen atom or a $C_1$-$C_4$ alkyl group, $R_9$ represents a hydrogen atom and B represents a cyano or a $C_2$-$C_5$ alkoxycarbonyl group, or $R_9$ and B taken together represent a

group, wherein W represents an oxygen atom or an imino group;

A represents a group of the formula $CH_2$, $CH_2CH_2$ or $CH=CH$; and n is 0, 1 or 2;

or a pharmaceutically acceptable salt thereof.

3. A compound according to claim 1 which is 6-methyl-8β-[(1H,3H)-2,4-dioxo-dihydro-1-pyrimidinylmethyl]-ergoline, or a pharmaceutically acceptable salt thereof.

4. A compound according to claim 1 which is 6-methyl-8β-[2,4-dioxo-1-imidazolidinylmethyl)-ergoline, or a pharmaceutically acceptable salt thereof.

5. A compound according to claim 1, which is:
6-methyl-8β-[N-(2-methoxycarbonylethyl)-N-carbamoyl-aminomethyl]-ergoline,
6-methyl-8β-[N-(2-methoxycarbonylethyl)-N-methylcarbamoyl-aminomethyl]-ergoline,
6-methyl-8β-[(1H,3H)-2,4-dioxo-3-methyl-dihydro-1-pyrimidinyl-methyl]-ergoline,
6-methyl-8β[N-ethoxycarbonylmethyl-N-methylcarbamoyl-aminomethyl)-ergoline,
6-methyl-8β-(2,4-dioxo-3-methyl-1-imidazolidinyl-methyl)-ergoline,
6-methyl-8β-[N-(2-methoxycarbonylethyl)-N-propylcarbamoyl-aminomethyl]-ergoline,
6-methyl-8β-[(1H,3H)-2,4-dioxo-3-propyl-dihydro-1-pyrimidinyl-methyl]-ergoline,
6-methyl-8β-[N-(2-methoxycarbonylethyl)-N-isopropyl-carbamoyl-aminomethyl]-ergoline,
6-methyl-8β-[(1H,3H)-2,4-dioxo-3-isopropyl-dihydro-1-pyrimidinyl-methyl]-ergoline,
6-methyl-8β-[N-ethoxycarbonylmethyl-N-propylcarbamoyl-aminomethyl]-ergoline,
6-methyl-8β-(2,4-dioxo-3-propyl-1-imidazolidinyl-methyl)-ergoline,
6-methyl-8β-(N-ethoxycarbonylmethyl-N-isopropyl-carbamoyl-aminomethyl)-ergoline,
6-methyl-8β-(2,4-dioxo-3-isopropyl-1-imidazolidinyl-methyl)-ergoline,
6-methyl-8β-{2-[(1H,3H)-2,4-dioxo-dihydro-1-pyrimidinyl]-ethyl}-ergoline,
6-methyl-8β-[2-(2,4-dioxo-1-imidazolidinyl)-ethyl]-ergoline,
6-methyl-8β-[(1H,3H)-2,4-dioxo-dihydro-1-pryimidinyl]-ergoline,
6-methyl-8β-(2,4-dioxo-1-imidazolidinyl)-ergoline,
1,6-dimethyl-8β-[(1H,3H)-2,4-dioxo-dihydro-1-pyrimidinyl-methyl]-ergoline,
1,6-dimethyl-8β-(2,4-dioxo-1-imidazolidinyl-methyl)-ergoline,
6-methyl-10-methoxy-8β-(2,4-dioxo-1-imidazolidinyl-methyl)-ergoline,
6-methyl-8β-[(1H,3H)-2,4-dioxo-1-pyrimidinyl-methyl]-ergoline,
6-methyl-8β-[(1H)-2-thioxo-4-oxo-tetrahydro-1-pyrimidinyl-methyl]-ergoline,
6-methyl-8β-[(1H)-2-thioxo-4-oxo-3-methyl-tetrahydro-1-pyrimidinyl-methyl]-ergoline,
6-n-propyl-8β-[(1H)-2-thioxo-4-oxo-3-methyl-tetrahydro-1-pyrimidinyl-methyl]-ergoline,
6-allyl-8β-[(1H)-2-thioxo-4-oxo-3-methyl-tetrahydro-1-pyrimidinyl-methyl]-ergoline,
6-methyl-8β-(2-thioxo-4-oxo-3-methyl-1-imidazolidinyl-methyl)-ergoline,
6-propyl-8β-(2-thioxo-4-oxo-3-methyl-1-imidazolidinyl-methyl)-ergoline,
6-allyl-8β-(2-thioxo-4-oxo-3-methyl-1-imidazolidinyl-methyl)-ergoline,
6-methyl-8β-[N-(2cyanoethyl)-N-carbamoyl-aminomethyl]-ergoline,
6-methyl-8β-[(1H,3H)-2-oxo-4-imino-dihydro-1-pyrimidinyl-methyl]-ergoline, 2-bromo-6-methyl-8β-(2,4-dioxo-1-imidazolidinyl-methyl)-ergoline,
2,6-dimethyl-8β-(2,4-dioxo-1-imidazolidinyl-methyl)-ergoline,
2-thiomethyl-6-methyl-8β-(2,4-dioxo-1-imidazolidinyl-methyl)-ergoline,
6-n-propyl-8β-(2,4-dioxo-1-imidazolidinyl-methyl)-ergoline,
6-methyl-8α-(2,4-dioxo-1-imidazolidinyl-methyl)-ergoline,
6-methyl-8-[(1H,3H)-2,4-dioxo-dihydro-1-pyrimidinyl-methyl]-8,9-didehydro-ergoline,
6-methyl-8-(2,4-dioxo-1-imidazolidinyl-methyl)-8,9-didehydro-ergoline,
6-methyl-8β-[(1H,3H)-2,4-dioxo-dihydro-1-pyrimidinyl-methyl]-9,10-didehydro-ergoline, or
6-methyl-8β-(2,4-dioxo-1-imidazolidinyl-methyl)-9,10-didehydro-ergoline,
or a pharmaceutically acceptable salt thereof.

6. A pharmaceutical composition for lowering blood pressure comprising a therapeutically effective amount of a compound of claim 1 or a pharmaceutically acceptable salt thereof in admixture with a pharmaceutically acceptable diluent or carrier.

7. A method for lowering blood pressure in a human which method comprises administering to a subject in need of such treatment a therapeutically effective amount of the compound of claim 1 or a pharmaceutically acceptable salt thereof or a pharmaceutical composition containing a therapeutically effective amount of the compound of claim 1 or a pharmaceutically acceptable salt thereof.

* * * * *

UNITED STATES PATENT AND TRADEMARK OFFICE
CERTIFICATE OF CORRECTION

PATENT NO.  : 4,690,929

DATED       : September 1, 1987

INVENTOR(S) : Luigi Bernardi et al.

It is certified that error appears in the above-identified patent and that said Letters Patent is hereby corrected as shown below:

Title of invention should read -- ERGOLINES EXHIBITING PROLACTIN SECRETION INHIBITION ACTIVITY --.

Signed and Sealed this

Twenty-second Day of December, 1987

Attest:

DONALD J. QUIGG

*Attesting Officer*  *Commissioner of Patents and Trademarks*